United States Patent [19]

Ray

[11] Patent Number: 4,975,981

[45] Date of Patent: Dec. 11, 1990

[54] SLIP-ON FACE SHIELD

[75] Inventor: Michael A. Ray, Louisville, Ky.

[73] Assignee: Borden, Inc., Columbus, Ohio

[21] Appl. No.: 396,310

[22] Filed: Aug. 21, 1989

[51] Int. Cl.⁵ .............................................. A42B 1/06
[52] U.S. Cl. ............................................... 2/10; 2/171;
2/173; 2/185 R; 2/199; 2/424
[58] Field of Search .................... 2/10, 171, 173, 174,
2/185 R, 199, 424, 425

[56] References Cited

U.S. PATENT DOCUMENTS

| 1,104,553 | 7/1914 | Scaturro | 2/424 |
|---|---|---|---|
| 1,164,351 | 12/1915 | Hulström | 2/10 X |
| 1,183,385 | 5/1916 | Kunstadter | 2/10 X |
| 1,222,995 | 4/1917 | Rhoades | 2/10 X |
| 1,695,596 | 12/1928 | Levinsky | 2/10 |
| 2,184,240 | 12/1939 | McInnis | 2/174 |
| 2,462,679 | 2/1949 | Rosenau | 2/199 X |
| 2,631,286 | 3/1953 | Bowers | 2/10 X |
| 2,677,457 | 5/1954 | Guest | 2/199 X |
| 3,113,321 | 12/1963 | Siegel | 2/174 |
| 3,138,801 | 6/1964 | Brodsky | 2/174 |
| 3,314,079 | 4/1967 | Stout et al. | 2/173 |
| 3,668,705 | 6/1972 | Garbisch | 2/10 |
| 3,685,054 | 8/1972 | Raschke | 2/10 |
| 4,272,853 | 6/1981 | Schuessler | 2/424 |
| 4,329,742 | 5/1982 | Schuessler | 2/424 |
| 4,547,908 | 10/1985 | Karlsson et al. | 2/10 X |
| 4,683,596 | 8/1987 | Cole | 2/174 |
| 4,850,049 | 7/1989 | Landis et al. | 2/10 |
| 4,852,186 | 8/1989 | Landis . | |

FOREIGN PATENT DOCUMENTS

| 3730202 | 4/1989 | Fed. Rep. of Germany | 2/425 |
|---|---|---|---|
| 497387 | 12/1938 | United Kingdom | 2/175 |

OTHER PUBLICATIONS

Pages 73-75 or 1988 Lab Safety Supply catalog.
Pages 20-22 of a 1988 Sales Brochure of Orr Safety.

Primary Examiner—Werner H. Schroeder
Assistant Examiner—Jeanette E. Chapman
Attorney, Agent, or Firm—Sidney W. Millard

[57] ABSTRACT

A flexible dome-shaped cap is connected to a face shield and is designed to slip over a hard hat. The face shield fits in place to temporarily protect the wearer from splashing liquids and solid particles.

5 Claims, 1 Drawing Sheet

U.S. Patent     Dec. 11, 1990     4,975,981
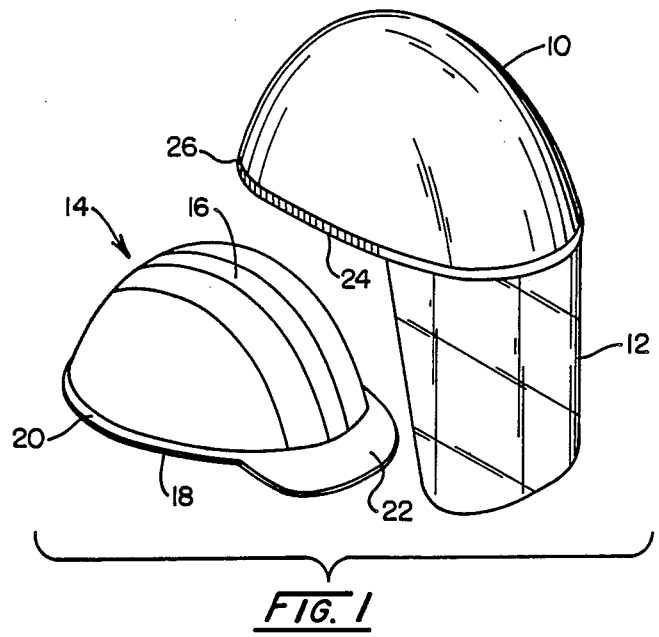
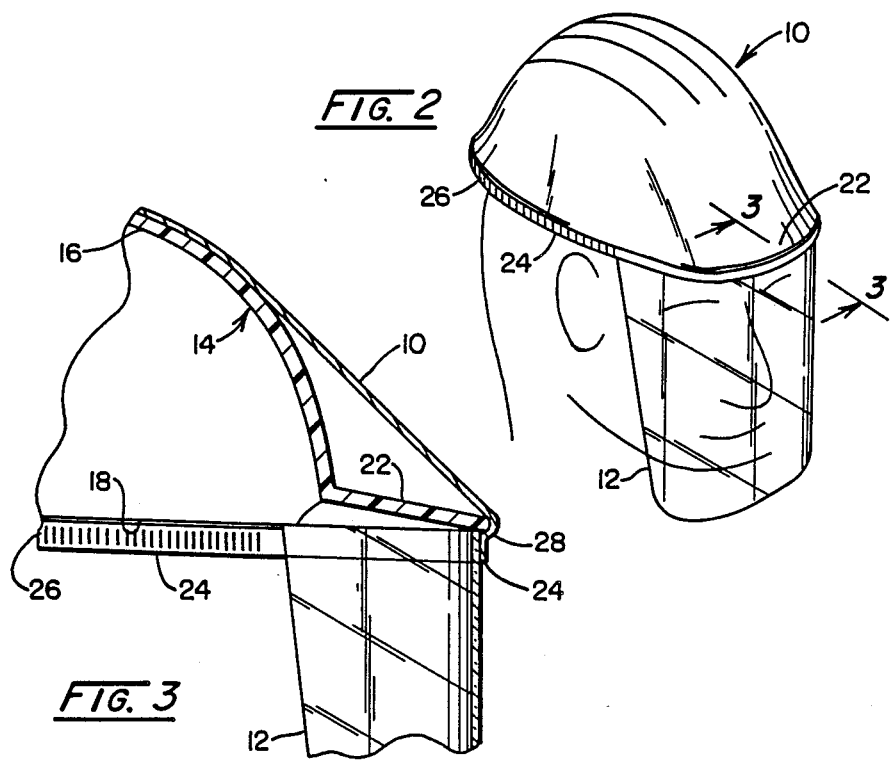

SLIP-ON FACE SHIELD

FIELD OF THE INVENTION

This invention relates to a cap and face shield for fitting over a hard hat, which cap and shield are fluid impervious.

BACKGROUND OF THE INVENTION

In some industrial and laboratory environments workers are exposed to corrosive or contaminating liquids or sometimes solid particles as may occur in welding, abrading, grinding and the like. For industrial safety, workers are usually required to wear goggles and/or use shields between their upper body and head and the liquid or solid source of potential worker injury.

A special example of a protective shield is the hood used in electric arc welding situations. Hoods include a head band which ordinarily fits around the head of the welder who may or may not have a cloth cap to cover his head. The hood itself is attached to the head band and is similar in shape to half of a hollowed out watermelon. A slit at eye level through the hood provides an opening for the welder to view the electric arc. The eye level slit is covered by a rectangle of blackened glass, polycarbonate, cellulose polyonate, acetate or the like. The glass rectangle is darkened to shield the welder's eyes from the bright light of the arc. The object of the large hood is to protect the face and neck of the welder from sparks. If a hat is worn it is usually wool because wool will not burn whereas cotton will smolder and burn.

Usually gas welding will only use a set of goggles to protect the eyes of the welder because there is not such a proliferation of sparks as occurs with electric welding.

When using corrosive chemical materials (usually liquid), workers are often required to wear face shields which extend from forehead to below the chin and those shields are often composed of clear polycarbonate or the like. The means for attaching the face shield to the head of the worker is essentially the same as is used with hoods of welders used in electric arc welding, namely, adjustable head bands.

In some industrially used apparatus a face shield which is vertically tiltable is rigidly mounted on a "hard hat". A hard hat is a plastic or metal head covering worn by workers in areas where there is a potential for objects being dropped from above. The hard hat is intended to prevent the worker from being badly injured because of something dropping onto his head from above. Attaching a heavy polycarbonate face shield to a hard hat which a worker must wear all during his shift of work is merely one more physically tiring burden to be borne by the worker. Worker fatigue is to be avoided because it is a contributing factor in many industrial accidents.

In addition to the weight of the face shield in combination with the hard hat, the connection which allows the face shield to be tilted upward out of the line of sight of the worker also creates an inherent problem from a safety standpoint. The shield is allowed to tilt because it is not connected along the bill of the hard hat. Should acid splash on the worker, the shield will prevent its direct impact on his face or eye. However, if the acid lands on the front or top of the hard hat it will run down the slope until it drips off the bill of the hard hat and possibly onto the nose or other part of the worker's face. Conventional shields prevent straight line impact; they are not designed to shield against drops running down the hard hat.

SUMMARY OF THE INVENTION

This invention solves these problems. It provides a light weight removable face shield which will fit over the top of a hard hat. Thereby a worker who is required to wear a hard hat at all times, but only occasionally a face shield, could use this invention to avoid wearing the heavy face shield at all times. When the worker leaves the corrosive liquid area the shield can be slipped off and left for another.

Additionally, the apparatus of this invention provides a thin flexible dome-shaped plastic cap to fit over the metal or plastic hard hat and extend below the lower edge of the hard hat where an elastomeric edging will hold the cap in place. At the front of the flexible cap is a shield curved to fit around the face of the worker and with the bill of the hard hat serving to hold the cap and shield in position such that the shield hanging vertically will be out of direct physical contact with the face of the worker. The connection holding the bottom edge of the cap to the face shield is so structured as to be liquid impervious. Thereby when acid or the like is splashed onto the top of the head of the worker, the acid will run down the outer surface of the cap, past the connection between the cap and face shield and down the outside of the face shield rather than inside the face shield as is inherent with the prior art apparatus.

Objects of the invention not obvious from the above will be clear from a review of the drawings and the description of the preferred embodiment which follows.

BRIEF DESCRIPTION OF THE DRAWINGS

FIG. 1 is an exploded view of a flexible cap and relatively rigid shield of this invention in combination with a hard hat;

FIG. 2 is a perspective view of the cap and shield combination pulled into operative position over a hard hat; and FIG. 3 is a fragmentary sectional view taken along lines 3—3 of FIG. 2 and showing the structural relationship between the bill of the hard hat, the face shield and the flexible cap.

DESCRIPTION OF THE PREFERRED EMBODIMENT

FIG. 2 illustrates a thin flexible cap 10 having a face shield 12 mounted over a conventional hard hat 14. FIG. 1 shows an exploded view of the combination of FIG. 2.

A conventional hard hat is constructed of metal or hard plastic and is designed to withstand some minimal impact from rocks, tools and the like which may accidentally fall from above and strike the head of the wearer. The internal structure of the hard hat includes an adjustable band which fits around the head of the wearer and a harness fitting over the top of the wearer's head to hold the outer hard hat structure away from the head to again minimize impacts. The internal structure of the hard hat is conventional, is not a part of this invention, and is not illustrated.

The hat itself includes a crown portion 16 and about its lower edge 18 is an outwardly flaring deflecting flange 20. A bill 22 projects forwardly from the front of the hat above the level of the eyes of the wearer. The purpose of the bill 22 is to provide a greater protection from vertically falling objects at the point of the eyes of the worker.

The slip-on cap 10 of this invention is a generally dome-shaped thin plastic material which is liquid impervious and is designed to fit over the dome-shaped crown 16 of the hard hat. The extent of the dome-shape of the cap 10 is such that its bottom edge 24 will be lower than the lower edge 18 of the hard hat when the cap and shield combination are pulled into operative position, best seen in FIGS. 2 and 3.

To hold the cap and shield combination in operative position after it is donned, an elastomeric band 26 is provided around at least a part of the bottom edge 24 of the cap. Thereby, the elastomeric band 26 will contract below the lower edge 18 of the hard hat to hold the cap and shield in place. At rest the cap itself may look somewhat like a shower cap and the general shape of the attached shield is about the same as any conventional face shield.

Note in FIG. 3 that the bottom edge 24 of the cap is below the bottom of bill 22 and the fluid impervious connection 28 is drawn slightly inward toward the face of the wearer below the bill 22. The bill 22 holds the face shield 12 outward out of direct physical contact with the face of the wearer when it is hanging vertically. Because the shield 12 is curved around the face and the elastomeric band 26 pulls it under bill 22, the shield will not flop back and forth when it is worn.

The face shield 12 may be of any transparent or semi-transparent material as needed and it could be polycarbonate, acetate or any other material suitable for whatever environment is desired. What is significant in this invention is the fact that the cap and shield may be striped from the hard hat when the wearer has completed his work adjacent an area where corrosive materials are being used. Thereby, the worker does not have to change hard hats or make any physical adjustments to his everyday hard hat. The face shield and cap combination are easy to slip on and off and are calculated not only to minimize worker fatigue but also minimize worker burns by corrosive material which might ordinarily land on the crown of the hard hat and run down between the hard hat and the conventional pivotally mounted face shield. The fact that the cap 10 is fluid impervious will prevent corrosive materials from contacting the plastic or metal hard hat and the fluid impervious connection 28 between the cap 10 and the face shield 12 will prevent corrosive materials from dripping off the bill 22 of the hard hat between the bill and the pivotally mounted face shield.

Note that the face shield 12 is illustrated as curving from just forward of one ear to just forward of the other and from about the middle of the forehead to well below the chin. Splashing corrosive liquids should not be able to pass the shield and strike the face or neck of the worker. In some environments the chest, shoulders and arms will be covered with clothing and perhaps a protective apron. Industrial safety will be enhanced by this unique face shield combination because this combination bridges gaps in existing safety equipment and minimizes worker fatigue.

Having thus described the invention in its preferred embodiment, modifications will be obvious to those having ordinary skill in the art. It is not intended that the language used to describe the invention nor the drawings illustrating the same be limiting on the invention. Rather it is intended that the invention be limited only by the scope of the appended claims.

I claim:

1. A head and face shield comprising,
    a curved shield configured to extend (1) vertically from about the forehead of a wearer to below the wearer's chin and (2) horizontally in a curve around the wearer's face from about the forward edge of one ear to the other ear, said shield being impervious to liquids, whereby an object traveling in a straight line toward the face of the wearer must penetrate the shield before it strikes the face,
    means for holding the shield out of contact with the wearer's face,
    a cap for covering the top of the wearer's head above the wearer's ears, said cap comprising a flexible and fluid impervious material which is generally configured in the shape of a dome which is open at the bottom edge,
    a portion of the bottom edge of said cap being connected to the upper portion of said shield, said connection being fluid impervious whereby fluid draining from the exterior of the dome of the cap onto the shield will pass from the dome to the exterior surface of the shield,
    a portion of the bottom edge of the cap being elastomeric to allow flexibility of the cap during donning and removal of the shield and to flexibly hold the shield in place when it is on the wearer's head,
    the means for holding the shield out of contact with the wearer's face comprises a substantially rigid hat suitable for resting on the head of a wearer,
    said hat having a generally upwardly extending dome-shape with a lower edge, the bottom edge of the cap extending below the lower edge of the hat completely about its periphery to allow the elastomeric portion of the cap to contract inwardly below the lower edge of the hat.

2. The shield of claim 1 wherein said hat includes a forwardly projecting bill at the front to extend outwardly above the face of the wearer, the bottom of the cap connected to the shield extending below the bill of the hat to allow the elastomeric bottom edge of the cap to hold the cap in position on the hat.

3. The shield of claim 2 wherein the bottom edge of the cap extends below the lower edge of the hat and below the bill a distance less than will allow the shield to flop back and forth and impact on the nose of the wearer.

4. The shield of claim 1 wherein the bottom edge of the cap extends below the lower edge of the hat and below the bill a distance less than will allow the shield to flop back and forth and impact on the nose of the wearer.

5. The shield of claim 1 wherein the curved shield is rigid and transparent and is comprised of one of a material selected from the group consisting of polycarbonate and acetate.

* * * * *